(12) United States Patent
Gillis (10) Patent No.: US 6,455,272 B1
(45) Date of Patent: Sep. 24, 2002

(54) TESTING FOR BACTERIAL STERILIZING EFFECTIVENESS, AND TEST INDICATOR MANUFACTURE AND USE

(76) Inventor: John R. Gillis, 10 Evergreen Dr., Suite E, Bozeman, MT (US) 59715

(*) Notice: Subject to any disclaimer, the term of this patent is extended or adjusted under 35 U.S.C. 154(b) by 0 days.

(21) Appl. No.: 09/928,626

(22) Filed: Aug. 13, 2001

Related U.S. Application Data (63) Continuation-in-part of application No. 09/190,823, filed on Nov. 12, 1998, now Pat. No. 6,340,590.

(51) Int. Cl.⁷ ............................................. C12Q 1/22
(52) U.S. Cl. .................... 435/31; 422/58; 422/82.09
(58) Field of Search ......................... 435/31, 287.4, 435/288.7, 822; 422/58, 82.05, 82.09; 116/101, 206, 207, 216; 73/25.01

(56) References Cited

U.S. PATENT DOCUMENTS

| | | | |
|---|---|---|---|
| 4,311,793 A | * 1/1982 | Halleck | 435/287.4 |
| 4,353,990 A | * 10/1982 | Manske et al. | 116/207 |
| 5,073,488 A | * 12/1991 | Matner et al. | 435/31 |
| 5,223,401 A | * 6/1993 | Foltz et al. | 422/101 |
| 5,418,167 A | * 5/1995 | Matner et al. | 422/55 |
| 5,529,931 A | * 6/1996 | Narayan | 116/207 |
| 5,795,730 A | * 8/1998 | Tautvydas | 435/252.5 |
| 6,340,590 B1 | * 1/2002 | Gillis | 422/58 |

* cited by examiner

Primary Examiner—David A. Redding
(74) Attorney, Agent, or Firm—Shanley and Baker; Raymond N. Baker (57) ABSTRACT

Multiple early-load-release evaluations of sterilizing effectiveness for both "dry" and "wet" sterilizer loads, are made available by selective spectroscopic quantitative measurements of peak absorption of electromagnetic radiation, in selected UV and visible-light wavelength spectra developed for evaluating thermally-responsive change, in a fluid-state indicator material, which is correlated with the sterilizing effect of a selected cycle on bacterial spores of a sterilizer load. Biological evaluation of sterilizing effectiveness is made available with the same test devices, free of the risk of contamination, by measuring peak absorption of electromagentic radiation at developed wavelength spectra which evaluate pH change, if any, due to spore-growth, or the absence thereof, following a predetermined spore incubation period subsequent to completion of the thermal sterilizing cycle.

4 Claims, 6 Drawing Sheets

FIG. 12

TESTING FOR BACTERIAL STERILIZING EFFECTIVENESS, AND TEST INDICATOR MANUFACTURE AND USE

RELATED APPLICATIONS

This application is a continuation-in-part of copending and co-owned U.S. patent application Ser. No. 09/190,823 filed Nov. 12, 1998, now U.S. Pat. No. 6,340,590, issued Jan. 22, 2002

INTRODUCTION

This invention relates to evaluating bacterial sterilizing effectiveness of a thermal sterilizing cycle. In particular, this invention is concerned with embodiments of a sterility test indicator which individually can provide multiple early evaluations of bacterial spore sterilizing effectiveness, available directly upon completion of a saturated-steam sterilizing cycle, and, further, provide for incubation of potentially living bacterial spores, if any, for biological verification of sterilizing effectiveness.

OBJECTS OF THE INVENTION

A primary object is establishing test indicator constituents which respond to incrementally timed exposure, at a saturated steam temperature of a selected sterilizing cycle, which response is correlated with effectiveness of spore kill in a sterilizer load exposed to the same cycle.

A related object is providing for reliable quantitative measurements of peak absorption of selectively designated spectra of UV and visible-light electromagnetic radiation, which enable evaluations of thermal sterilizing effectiveness directly upon completion of a thermal sterilizing cycle, for prompt and safe release of a sterilizer load, free of a time-delay requirement for potential spore incubation.

A further related object is establishing electromagnetic radiation providing for peak absorption measurements at designated wavelength spectra, for the incremental effects of timed/temperature exposure on soluble constituents, of an indicating material, which are correlated with spore kill of a thermal load sterilizer.

An additional related object is providing fabricating materials for sterility test devices capable of withstanding evacuation of air from a sterilizing chamber for introduction of saturated steam at sterilizing temperature, and providing for transmission of electromagnetic radiation at specified wavelength spectra for multiple evaluations of sterilizing effectiveness.

The above and other advantages and contributions of the invention are considered in greater detail with references to the accompanying drawings.

DETAILED DESCRIPTION OF THE INVENTION

Figure 1:
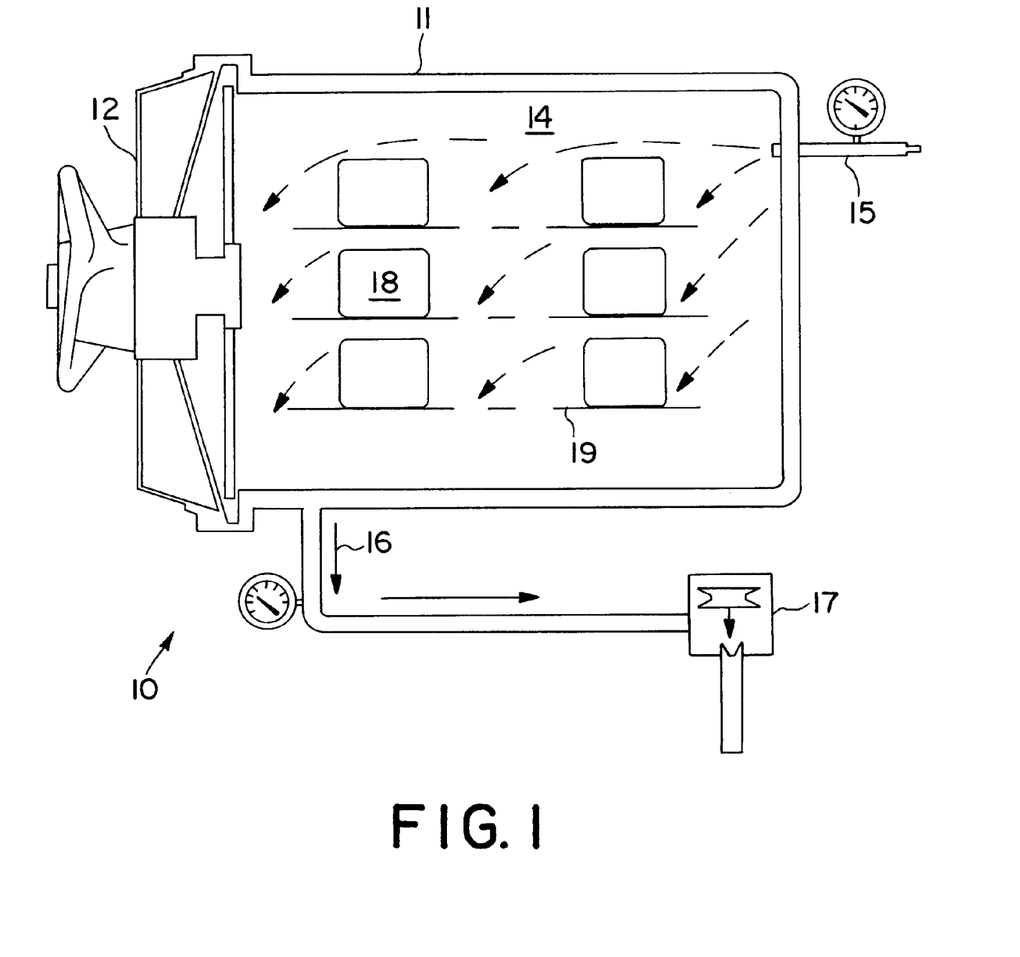
FIG. 1 is a schematic cross-sectional view in elevation, with portions cut away, of thermal sterilizing equipment for describing use of sterility test indicators of the invention which evaluate thermal bacterial sterilizing effectiveness.

Referring to FIG. 1, thermal sterilizer 10 includes steam jacket 11 and closure 12, which define an enclosed sterilizing chamber 14. Saturated steam is introduced at 15; air is removed at 16 by using, for example, a thermostatic valve mechanism 17.

Goods to be sterilized, of either a "dry" or "wet" goods sterilizer load, are represented at 18. Such goods are arranged on sterilizer racks, such as 19, for augmenting proper dispersing of incoming saturated steam, from inlet 15, throughout chamber 14.

"Dry goods" comprise surgical instruments, clothe, and like items used in surgery, which generally comprise a "dry-goods-load" for use of a test device embodiment of the invention. Bottled medicinal (parenteral) liquids form a "wet" load; and utilize a "wet-goods-load" test device embodiment of the invention.

Direction of movement of saturated steam within a sterilizing chamber, such as 14 of FIG. 1, and heat transfer principles are taken into account in placing sterility test units of the invention at various locations in association with goods to be sterilized. Size is a factor in manufacturing each test unit embodiment; and, is predetermined to permit proper placement of individual test devices in hard-to-heat, hard-to-steam portions of load items, in sufficient quantities to achieve reliable assurance of thermal exposure throughout a full sterilizer load to achieve spore kill.

Hospital and so-called "industrial" sterilizing organizations had, in the past, employed various specified-temperature melt items in testing for thermal sterilizer results. However, those sterilizing organizations have come to rely on strips, carrying bacterial spores, for a biological indication of sterilizing effectiveness. That is, relying on growth of spores, under spore culturing conditions, for indicating a lack of desired sterilizing effectiveness.

Reliable biological-indicator spore-strip methods have required extended incubation periods, for example, of more than two days and up to about seven days, following a thermal sterilizing cycle; in general the goods were to be quarantined in order to determine whether living spores, if any, survived the thermal cycle. Dependence on such biological means can cause significant delays before properly-authorized release of a load, especially, if added or repeated sterilizing efforts are required. Such delays create inventory supply hardships, especially for hospitals and the like.

Recognizing a need for developing a more-readily-operable sterility test material which can provide for scientifically-reliable early-load-release measurements; and also provide for subsequent biological verification, are contributions resulting from combinations of materials, assembly methods, and method of use of the invention.

Prompt multiple early-load-release evaluations of sterilizing effectiveness, and, the capability for biological verification of early-release evaluations, free of an opportunity for external contamination, are combined in the invention.

Figure 2:
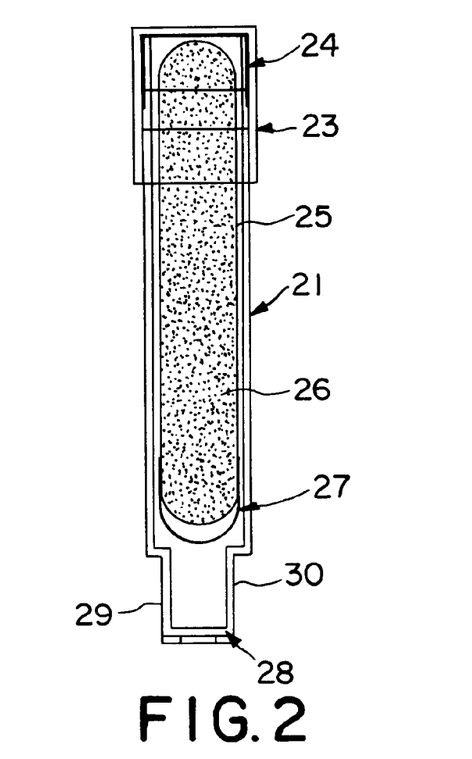
FIG. 2 is an enlarged schematic view, in cross section, of test indicator embodiment of the invention for describing a "dry-goods" application of the invention.
Figure 3:
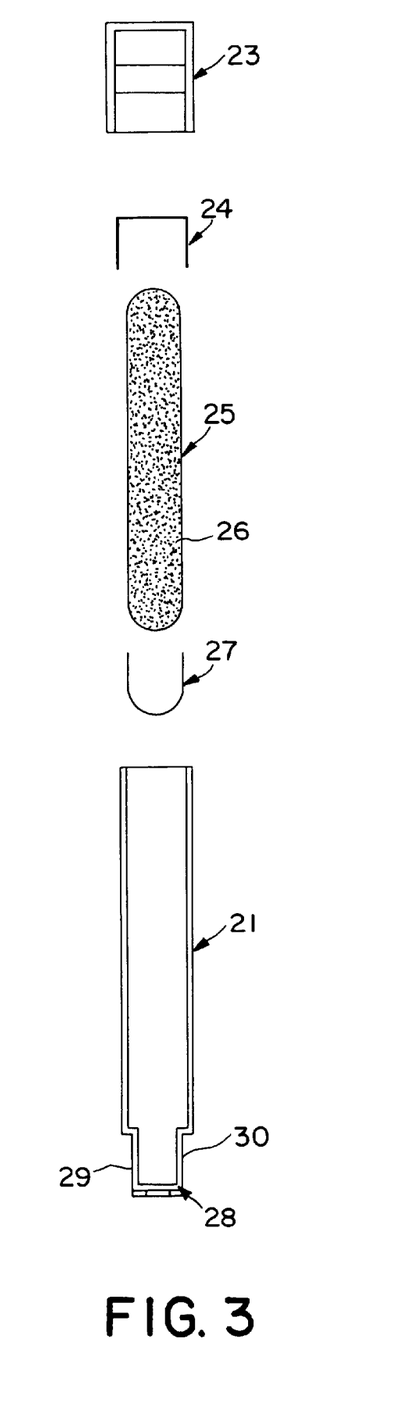
FIG. 3 is a pre-assembly view of the embodiment of FIG. 2 for describing fabricating methods and materials for components of test devices of the invention.

Test device 20 of FIG. 2 is used for testing a dry-goods-load for sterilization effectiveness. A pre-assembly view of test device 20 is shown in FIG. 3. An elongated one-piece container 21 is formed from a selected polymeric material which is impermeable to penetration of liquid, gas or bacterial spores, and also selected for electromagnetic radiation transmitting characteristics, for specified UV and visible light spectra for sterilizing effectiveness evaluations, so as to be substantially free of a requirement to compensate for specified peak absorption measurement wavelengths.

Multiple spectroscopic peak absorption measurements of sterilizing effectiveness are made available directly upon completion of a sterilizing cycle, so as to enable early and safe release of a sterilizer load; or, to promptly-determine need for added sterilizing efforts.

Referring to FIGS. 2 and 3, open end 22 of elongated one-piece container 21 is closed with a polymeric closure cap 23, selected to provide a closed structure physically capable of withstanding vacuum evacuation of air from a sterilizing chamber, as well as exposure to saturated steam at a temperature, and for a time, required for sterilization throughout a load.

Surgical-grade kraft paper filter 24 within closure cap 23 (FIGS. 2, 3), provides a tortuous-path cross section which prevents passage of spores and liquid into the capped container. An elongated sealed-glass capsule 25, holds indicator material 26 with constituents of the invention, for spectrographic peak absorption measurements, as set forth below. Sealed glass capsule is encapsulated within the elongated combination of tubular container 21 and closure cap 23. Spore paper 27, which presents an extended surface-area, is located across the entrance to a smaller-lateral-cross-sectional area comprising the unitary closed end of container 21, which presents convex-configuration 28.

Figure 6:
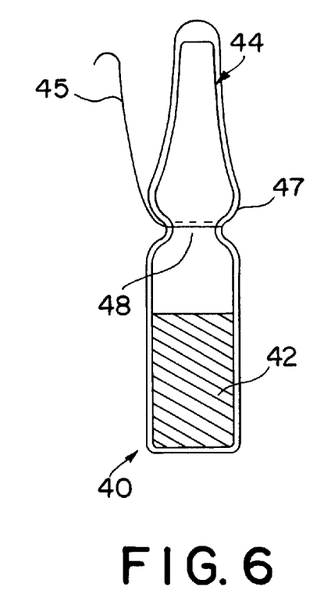
FIG. 6 is an enlarged schematic view, in cross section, of a test indicator embodiment of the invention for measuring bacterial sterilizing effectiveness on medicinal liquids within glass containers forming a sterilizer load, for describing a "wet-goods" application of the invention.

Sterility test units are fabricated with dimensions and configuration, so as to enable placement at desired test locations; and, for distribution of sufficient devices for testing throughout an entire sterilizing chamber load; also, such size and configuration, are selected to facilitate handling for spectroscopic analyses with later described equipment. The dry-goods-load test device as depicted by FIGS. 2, 3, 4 and 5, has an overall length of about one and seven eights inches, a cylindrical sidewall diameter of about $15/64$ inch for container 21, a closure cap diameter of about $3/8$ inch; encapsulated capsule 25 has a diameter of $7/32$ and at a length of one and nine sixteenth inches. Dimensions for a "wet" load test unit as shown in FIG. 6 are described, along with special liquid-load requirements, later herein. Preferably highly resistant organisms, such as B.stearothermophilus spores, with populations above about one million are used in test devices of the invention.

Figure 7:
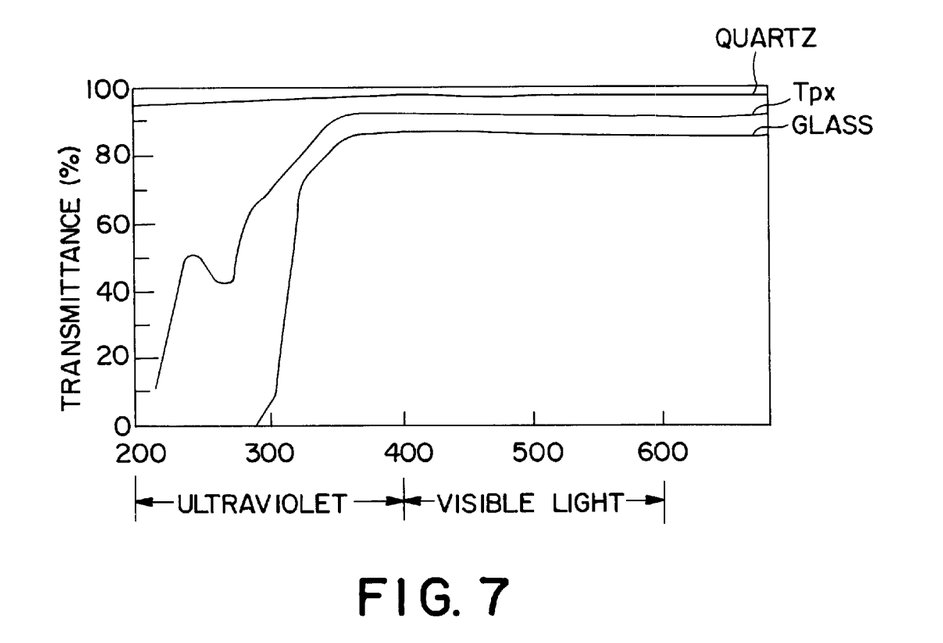
FIG. 7 is a graphical presentation of electromagnetic radiation transmission characteristics, of selected test device fabricating materials, covering specified measurement wavelength spectra of the invention.

Electromagnetic radiation transmission characteristics for preferred fabricating materials selected, as part of the invention, are described in relation to FIG. 7. Fabricating materials include quartz, a suitable borosilicate-type glass, and a suitable polymeric material. Quartz provides uniform transmissions characteristics for any of the specified spectra wavelengths for the specific embodiments of the invention being described. However, economically, quartz is largely limited to lab and "standards" development usage. Glass with low-expansion thermal characteristics capable of withstanding required temperature changes, has specific exterior barrier advantages for the "wet-goods-load" test device of FIG. 6, and, provides capabilities for peak absorption measurements concentrated in specified electromagnetic radiation wavelengths above about 300 nm.

A preferred polymeric material for container 21 FIG. 2 is TPX polymethylpentene, that polymer provides transmission characteristics selected for peak absorption measurements within specified spectra covering measurements for embodiments of the invention; those spectra include: about 260 nm, about 325 nm, about 430 nm, and about 590 nm.

TPX as depicted in FIG. 7, is preferred for transmission characteristics; other structurally-suitable polymers can be computer- compensated for lesser transmission characteristics for certain spectra, of the invention, if required.

Predetermined constituents soluble within a fluid state indicator material of the invention have been selected and combined to provide a response to thermal exposure which is correlated with bacterial spore kill within a load, concurrently experiencing the same thermal exposure.

Peak absorption spectroscopic measurements at designated wavelength spectra, as taught herein, accurately measure change of such constituents, responsive to saturated-steam temperature, and the time at temperature of the selected cycle. The fluid-state indicator material of the invention comprises a predetermined composition, of soluble simple and complex carbohydrates, which also provides growth nutrient for later biological evaluations, determined by spectroscopic measurement of the presence or absence of bacterial spore growth. Such soluble carbohydrates are charred incrementally in response to timed exposure at the saturated steam temperature of the selected cycle. Such carbohydrates have been selected in a manner such that the incremental change response is correlated with spore kill within a load experiencing the same time-at-temperature exposure.

Such correlated change of the carbohydrates is determined by peak absorption measurements at specified electromagnetic radiation wavelengths at about 260 nm and about 325 nm.; which provide evaluations of sterilizing effectiveness directly upon completion of a cycle, free of a delay for cultured spore growth. Such spectroscopic peak absorption measurements provide for reliably repeatable accuracy. Both such spectra (about 260 nm and about 325 nm)can be measured through the TPX polymeric barrier material of container 21 (FIG. 2). A sealed glass barrier of FIG. 7 enables peak absorption measurements at wavelength spectra above about 300 nm.

A further constituent of the indicator material of the invention provides an early-release evaluation and later biological evaluations. A soluble organic pH indicator is selected, which does not inhibit spore growth and which is not toxic to cells resulting from culturing live spores embodiments being described. The selected organic pH indicator constituent, responds incrementally to time at temperature in a manner believed to be due to shifting of shared electrons of ring components of the organic material. That the pH indicator provides an early load-release evaluation.

That change of the preferred bromcresol purple pH indicator is accurately correlated with spore kill in the load for early evaluations, by peak absorption measurements at a specified electromagnetic radiation wavelength of about 590 nm. And, bromcresol purple further provides for later, subsequent to delay for cultural spore growth, if any, for biological verification at about 430 nm; and, the absence thereof at about 590 nm.

Figure 4:
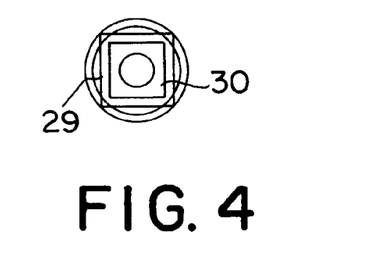
FIG. 4 is a bottom-plan view taken along line 4—4 of FIG. 2, at one longitudinal unitary end of a one-piece container of the "dry goods load" embodiment of the invention, shown in FIGS. 2 and 3.
Figure 5:
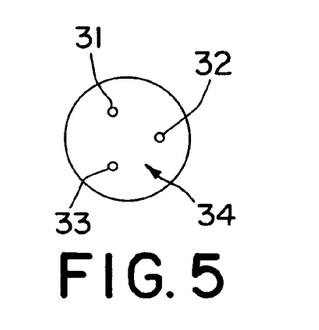
FIG. 5 is a top plan view, taken along line 5—5 of FIG. 2, for describing the longitudinally opposite end of the "dry-goods-load" embodiment of the invention, shown in FIGS. 2 and 3.

Referring to the dry load test embodiment of FIGS. 2–5, a preferred configuration for the convex configuration unitary end of one-piece 21 container is shown by the side elevational views of FIGS. 2, 3, and by the bottom plan view of FIG. 4. At such unitary end, convex configuration 28 has a smaller lateral cross-section, than that of the remaining side wall of tubular one-piece container 21. While other cross sectional configurations, than that shown, can be used, the rectilinear configuration shown at 28 is preferred because it presents substantially planar side walls, such as 29, 30, as shown by FIGS. 2, 3 and 4. The planar walls help to facilitate distortion-free transmission of electromagnetic radiation for specified peak absorption measurements.

The tortuous path cross section of paper liner 23, within the closure cap 22, is selected to prevent access of spores or liquids; while providing for desired saturated steam access through such small-dimensional apertures 31, 32, 33. As shown in the top plan view of closure cap end wall 34 of FIG. 5, desired access of saturation steam is accomplished by such distributed access providing a combined access area, which measures slightly less than about ten percent of end wall panel 34; the active nature of saturated steam at about 121° C. provides desired access.

That access of saturated steam provides thermal exposure for sealed glass capsule 25 and, the fluid-state indicator material contents 26 (FIG. 2). The saturated steam also travels longitudinally to expose bacterial spores on spore paper 27. Such provisions and exposure are selected to be substantially the same as that experienced by the load during designated steps of the selected saturated steam cycle.

The TPX polymeric material of one-piece container 21 is also selected for physical properties which enable fracturing of the sealed glass capsule 25 by distortion of container 21, while maintaining the sealing integrity of the above described capped container. Such fracturing is preferably carried out after thermal exposure, as individual test devices from a sterilization chamber are cooled to a uniform temperature; and, while the test devices are an upright position for evaluations. A uniform temperature is preferably selected at a designated culturing temperature, for spores, between about thirty five and about fifty five degrees centigrade.

The extended surface area of spore paper 27 is located at the entrance to such smaller lateral cross section convex configuration 28 unitary end of container 21. When capsule 25 is fractured, paper 27 prevents significant quantities of the fractured glass from descending into convex configuration 28, so as to prevent fractured glass from interfering with transmission of wavelengths of electromagnetic radiation, specified by the invention, for spectroscopic peak absorption measurements, in particular at less than about 300 nm.

In the embodiment of FIG. 6, spores within sealed borosilicate-type glass ampoule 40 are combined directly within the fluid state indicator material 42. The constituents of the invention, include a composition of simple and complex carbohydrates and an organic pH indicator as described above, to thermal exposure.

The sealed glass ampoule 40 is impermeable to liquid, gas and bacterial spores, and, with fluid-state indicator 42, can be submerged within a bottled liquid to a selected difficult-to-heat level; that is, for "wet" load testing of glass containerized injectable liquids, referred to "parenteral" solutions. The configuration of ampoule 40, with extended length portion 44 and contents 42, provides the necessary weight to enable ampoule 40 to be suspended by lanyard such as 45; so as to be submerged due to its own weight to a desired depth in a container for the medicinal liquid; such containers are typically made from borosilicate-type glass.

As described in relation to FIG. 7, the sealed glass exterior barrier for ampoule 40 enables peak absorption measurements for the charring effect of the carbohydrate composition at about 325 nm, and the early evaluation resulting from change in peak absorption due to the presence of the pH indicator is carried out at about 590 nm. Later biological indications for the effect of the timed/temperature cycle on spores rely on change or absence of change in pH of the indicator material, which are carried out after a spore culturing period at about 430 nm and about 590 nm, respectively.

The diameter of the main body of portion ampoule 40 (FIG. 6), which contains fluid-state indicator material 42, is about three eights of an inch; and a larger diameter bulb portion 47, above a restricted diameter 47, has a diameter of about nine thirty seconds inch; the overall length sealed glass ampoule 40 is about one and three quarter inches.

Quantitative measurements of chemical change due to thermal exposure of soluble carbohydrate constituents in the embodiment of FIG. 2, are carried out by spectroscopic measurement of peak absorption of electromagnetic radiation selected in a UV spectra of about 260 nm and about 325 nm; and the early evaluation of the effect on the preferred organic pH indicator is carried out in a visible light spectrum of about 590 nm. Such peak measurements are preferably made after the rupture of sealed glass capsule 25 of FIG. 2. The preferred rupture time of sealed glass capsule 25 is determined, at least in part, by the objective of providing the opportunity for a uniform culture temperature for spore growth, for biological verification of earlier evaluations. As set forth, growth of live spores, if any, in the indicator material of the invention is determined at about 430 nm; and measurements of the absence of such growth are carried out at about 590 nm. Glass and TPX have similar transmission characteristics for those spectra.

Bromcresol purple is the preferred pH indicator, of the invention. Spore growth raises the acidity and it has been found that a reading at about 430 nm is observable by spectroscope significantly earlier than any visible appearance of spore growth. When no spore growth occurs, there is no measurement at about 430 nm; however, a measurement, after an incubation period, at about 590 nm verifies the absence of spore growth. The availability those electromagnetic absorption measurements by spectroscope, has been found to significantly decrease the spore incubation period to less than two days, that is such peak absorption measurements (at about 430 nm and about 590 nm) are available in a matter of several hours rather than days, so as to shorten the time delay for biological verification of earlier-evaluations taken upon completion of the cycle.

In practice, peak absorption measurements of a specified spectrum can extend over a wavelength range which can depend on the filter means used in the spectroscopic equipment. For example: "about 260 nm" can have a peak absorption band of about 255 nm to about 265 nm; "about 325 nm" can extend from about 320 to about 330 nm; "about 430 nm" can extend from about 420 to about 440 nm; and, "about 590 nm" can extend about 580 to about 600 nm. However, in each of the above, the peak characteristic for measurement of absorption is clearly identified.

Properly opening a sterilizer chamber after completion of the saturated-steam cycle, causes steam to be immediately drawn off. However, the load and test devices can be near the sterilizing temperature. Decreasing the temperature of test devices to the desired uniform temperature can be a matter of minutes; however, as defined herein, that timing is within the terminology used in describing "early" evaluations or measurements "directly" upon completion designated steps of a sterilizing cycle, for indicating sterilizing effectiveness of that cycle.

Figure 8:
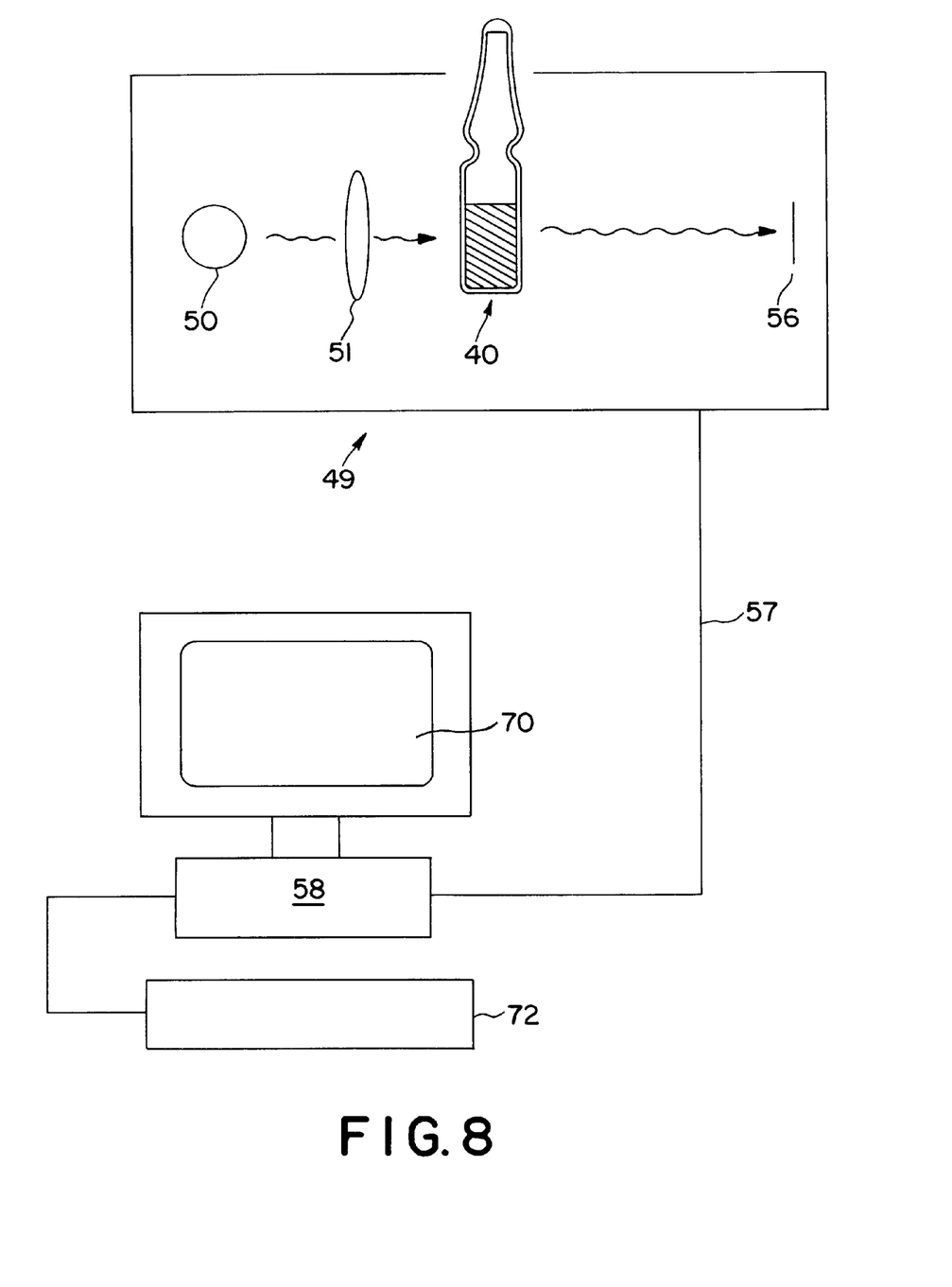
FIG. 8 is a schematic general arrangement view, partially in cross section for describing spectroscopic equipment, and measuring methods for load release evaluations using test indicator embodiments of the invention.

FIG. 8 schematically depicts a combination of components for facilitating spectroscopic absorption measurements, including microprocessor equipment. Spectrophotometer 49 utilizes electromagnetic radiation source 50, and filter 51 for selecting electromagnetic radiation in a spectra as previously described, for early-evaluations and later biological-verification, by measurement of a test unit 40. Such a test unit can be the "dry-goods" test device of FIG. 2 or a "wet goods" test device, such as 40, of FIG. 6.

A test device of the embodiment of FIG. 6 is ordinarily suspended by a lanyard similar to that used in suspending the test unit in a containerized liquid, as earlier described. A holder, for a dry-goods-load embodiment of FIG. 2, positions the convex-configuration portion, as previously described, so that the desired wavelength from filter 51 can be directed through that unitary closed portion of container 21.

Spectroscopic peak absorption measurements of a selected wavelength are carried out at detector 56; and, are directed through connector 57 for processing in computer 58. The latter can compensate for transmission characteristics, when using differing barrier materials. Computer 58 can also provide for viewing at video 70, of peak absorption readings, as measured, and, for printouts.

Data, such as sterilization temperatures, sterilizing test ampoule identification, information such as minimum values relating to desired sterility, type of goods to be sterilized, and other identification information, can be introduced manually through input keyboard 72. System software enables carrying out statistical functions and calculations, as well as graphic display on video 70 and printout capability.

Figure 9:
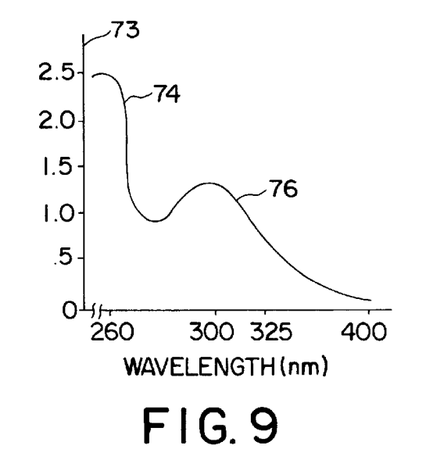
FIG. 9 is a graphical presentation for describing spectroscopic peak-absorption measurements of the invention for early-load-release evaluations of sterilizing effectiveness, utilizing specified UV and visible light electromagnetic radiation wavelength spectra selected in accordance with the invention.

Peak absorption measurement(s) at specified wavelength spectra, as described above, are shown graphically in FIGS. 9 through 12. FIG. 9 shows peak absorption measurements along "y" axis 73 at respective specified wavelength spectra of about 260 nm, at 74, and about 325 nm, at 76, of the carbohydrate composition, as described above and set forth in more detail later in Table 1. Both absorption measurements at 74 and 76 are available with the "dry goods" embodiment of FIG. 2 using the polymer TPX as the exterior barrier. Absorption measurements at about 325 nm are made with the borosilcate type of sealed-glass exterior "wet-goods" embodiment 40 of FIG. 7

Figure 10:
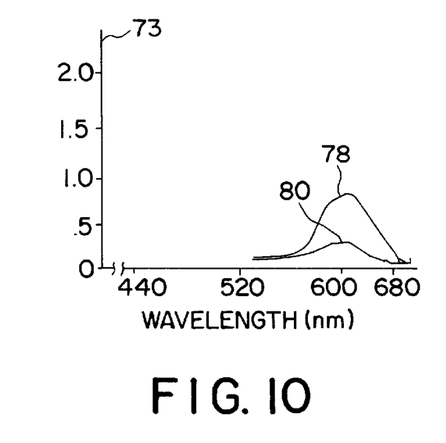
FIG. 10 is a graphical presentation for describing spectroscopic peak-absorption measurements of the invention, for further early-load-release evaluations of sterilizing effectiveness utilizing electromagnetic radiation of a visible light spectrum selected in accordance with the invention.

FIG. 10 shows peak absorption measurements along "y" axis 73 of the bromcresol purple pH indicator in the fluid state indicator material, measured for each embodiment (FIGS. 2 and 7) at about 590 nm. Upper line 78 in FIG. 10 indicates peak absorption due to the presence of bromcresol purple, as measured before thermal exposure. A diminished peak absorption, due to thermal exposure at timed/temperature of the selected cycle, is shown by solid line 80. Such decrease in peak absorption indicates spore kill in a sterilizer load experiencing the same thermal exposure, and is available directly upon completion completing designated steps of the selected cycle.

Figure 11:
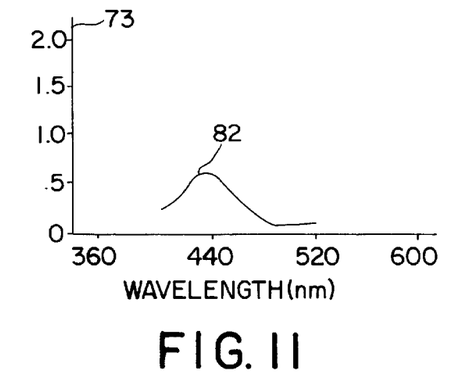
FIG. 11 is a graphical presentation for describing spectroscopic peak-absorption measurements of the invention, subsequent to a period for cultured spore growth, if any, for a biological indication, at a specified wavelength spectrum selected in accordance with the invention, for determining the presence of spore growth, if any.

FIG. 11 is for describing a change in pH in response to spore growth, after a predetermined culture period. Spore growth increases the acidity of the fluid-state indicator material, such change in pH is measured by peak absorption measurements along "y" axis 73, due to the presence of the bromcresol purple, which is measured at about 430 nm.

Figure 12:
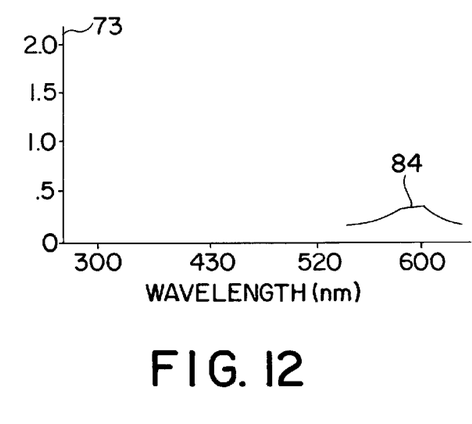
FIG. 12 is a graphical presentation for describing spectroscopic peak-absorption measurements at a selected wavelength spectrum of the invention, subsequent to a spore-growth culture period, for verifying the absence of spore growth in accordance with the invention.

The absence of spore growth, after an incubation period, is shown at 84 in FIG. 12, which is measured at about 590 nm shown.

Preferred carbohydrate and pH indicator constituents at the aqueous indication are tabulated below:

TABLE I

| CONSTITUENT CARBOHYDRATE | CONCENTRATION (Grams/Liter) |
|---|---|
| Tryptone | 8.5 |
| Glucose | 5.0 |
| Ceduna | 1.5 |
| Yeast Extract | 0.5 |
| Soluble Starch | 1.0 |
| PH INDICATOR | |
| Bromcresol Purple | 0.0024 |

TABLE II shows the timed exposure requirements for a dry-goods-loan with a cycle using saturated steam at 121° C.; a population of one million B. B.stearothermophilus spores are used in preferred embodiments of test device pf the invention.

TABLE II

Survival/Kill Results After Incubation/Dry-goods-load at 121° C.

| EXPOSURE TIME (MINUTES | PERCENTAGE OF INDICATORS HAVING LIVING SPORES (INCUBATION RESULTS) |
|---|---|
| 0 | 100% |
| 7 | 100% |
| 8 | 100% |
| 9 | 100% |
| 10 | 100% |
| 11 | 40% |
| 12 | 20% |

TABLE II-continued

Survival/Kill Results After Incubation/Dry-goods-load at 121° C.

| EXPOSURE TIME (MINUTES | PERCENTAGE OF INDICATORS HAVING LIVING SPORES (INCUBATION RESULTS) |
|---|---|
| 13 | 0% |
| 14 | 0% |
| 15 | 0% |
| 16 | 0% |
| 17 | 0% |

As shown by TABLE II, timed exposure of less than thirteen minutes, at 121° C. temperature, shows survival of spores for sterilizing practice. A total kill of all spores, should be found in all test devices distributed in a load, in order to confirm desired time/thermal exposure throughout the load.

A "wet goods" load using saturated steam at 121° C., requires significant increase in minimum timed exposure at that temperature. Thirty minutes can be a minimum requirement for parenteral liquids; however, an hour or more dependent on the size of the containers, can be required.

The early evaluations of sterilizing effectiveness can safely eliminate the delay of incubation and the quarantine time periods. That is, with a routinely cleansed and properly operating sterilizer, only randomly selected subsequent biological-cycle verification of multiple early-release evaluations need be considered.

Indicator materials and constituents, fabricating materials and configurations, measuring methods and apparatus, wavelengths, and other specifics have been set forth for purposes of describing the present invention and the manner of making and using that invention. However, it should be recognized that detailed specifics for carrying out the invention, and of principles of the invention, have been provided for those skilled in the art. And, in the light of the above teachings modifications can be devised for those specifics while continuing to rely on the basic concepts, principles, and materials disclosed above. Therefore, for purposes of determining the proper scope of patent protection, reference shall be had to the scope of the appended claims which are to be construed in the light of the teachings of the above teachings.

What is claimed is:

1. Method enabling multiple evaluations, utilizing a single sterility test device, of bacterial sterilizing effectiveness on a thermal sterilizer load after carrying out designated steps of a selected saturated-steam sterilizing cycle, comprising,
  A. providing a plurality of sterility test devices, each:
    (i) having a size and configuration enabling evaluations of sterilizing effectiveness by selecting at least one difficult-to-load location for placement of an individual test device for testing sterilizing effectiveness throughout such sterilizer load,
    (ii) containing an aqueous fluid-state indicator material with constituents which respond to steps of such cycle in a manner correlated to sterilizing effectiveness on bacterial spores of a load exposed to the same steps of such cycle,
    (iii) having an exterior barrier capable of transmitting electromagnetic radiation enabling spectroscopic peak absorption measurements of such fluid state indicator at specified wavelength spectra;
  B. providing for exposure, of such indicator material to such cycle, so as to enable selection from the group consisting of:
    (i) an early load-release evaluation of sterilizing effectiveness, which is available by:
      (a) quantitatively measuring peak absorption of electromagnetic radiation of specified wavelength spectra resulting from chemical change due to the presence of a predetermined composition of carbohydrates which comprises a growth nutrient for bacterial spores, in solution in such indicator material exposed to such cycle, with
      (b) at least one such peak absorption measurement due to such chemical change being available directly upon completion of such cycle utilizing an electromagnetic radiation wavelength in the UV spectra, so as to
      (c) provide an indication selected from the group consisting of:
        indicating to directly release such sterilizer load as exposed to steps of such cycle, and
        indicating added sterilizing efforts on such load should be required before such release;
    (ii) a further early-load-release evaluation of sterilizing effectiveness which is available by:
      (a) quantitatively measuring for peak absorption of electromagnetic radiation resulting from/the exposure of an organic pH indicator, in solution in such indicator material of such test devise exposed to such cycle,
      (b) which pH indicator is selected to avoid inhibiting later incubated spore growth, if any, and is non-toxic to cells resulting from any such spore growth, with
      (c) such peak absorption measurement due to presence of such pH indicator, being available directly upon completing such cycle, utilizing an electromagnetic radiation wavelength in the visible light spectrum, so as to,
      (d) provide an indication selected from the group consisting of:
        indicating a direct release of such sterilizer load as exposed to designated steps of such cycle, and
        indicating that added sterilizing efforts on such load should be required before such release;
  C. enabling a further evaluation of bacterial sterilizing effectiveness, by:
    (i) positioning live spores within such exterior barrier of such test devise so as to be capable of being exposed to steps of such cycle, so as to:
    (ii) provide for growth of live spores, if any, in such test device due to establishing contact with such carbohydrate composition which comprises a growth nutrient for spores following a predetermined culture period for spores.

2. Method enabling multiple evaluations, of bacterial sterilizing effectiveness of a sterilizer load after carrying out designated steps of a selected saturated-steam sterilizing cycle, comprising,
  A. providing an aqueous fluid-state indicator material with constituents in solution selected so as to respond incrementally to timed exposure to saturated steam temperature of such a cycle in a manner correlated with sterilizing effectiveness on bacterial spores of a sterilizer load exposed to such a cycle; such constituents including:

B. a predetermined composition of carbohydrates in solution in such indicator material, which
   (i) comprises a growth nutrient for bacterial spores,
   (ii) incrementally changes chemically with such timed-temperature exposure,
   (iii) produces a peak absorption measurement available directly upon completion of such cycle, utilizing an electromagnetic radiation wavelength spectra selected from the group consisting of about 260 nm and about 325 nm, so as to:
   (iv) provide an indication selected from the group consisting of:
      (a) whether to directly release such sterilizer load as exposed to steps of such cycle, and
      (b) whether added sterilizing efforts for on such load should be required before such release;
C. providing an organic pH indicator, in solution in such indicator material, which:
   (i) is capable of providing a peak absorption measurement of electromagnetic radiation, in a visible light wavelength spectrum of about 590 nm, which is available directly upon completing such cycle,
   (ii) is capable of evaluating sterilizing effectiveness so as to provide for an indication selected from the group consisting of,
      (a) whether to directly release such sterilizer load as exposed to designated steps of such cycle, and
      (b) whether added sterilizing efforts for such load should be required before such release;
D. providing potential for cultured growth of live spores, if any, exposed as to such a cycle, due to contact of test spores with such fluid-state indicator material containing such carbohydrate composition which comprises a growth nutrient for spores, and in which such organic pH indicator has been selected;
   (i) to avoid inhibiting growth of live spores, if any,
   (ii) is non-toxic to organic cells resulting from any such spore growth, and
   (iii) provides for a biological indication of sterilizing effectiveness based on pH of such fluid-state indicator material, by
      (a) quantitatively measuring for peak absorption of electromagnetic radiation in a wavelength spectrum selected for indicating an increase in acidity due to spore growth, if any, and
      (b) quantitatively measuring for peak absorption of electromagnetic radiation in a wavelength spectrum for indicating an absence of change of pH.

3. The subject matter of claim 1 or 2, in which such indicator material comprises an aqueous solution containing the following:

| CONSTITUENT | CONCENTRATION (Grams/Liter) |
| --- | --- |
| Carbohydrates | |
| Tryptone | 8.5 |
| Glucose | 5.0 |
| Soytone | 1.5 |
| Yeast Extract | 0.5 |
| Soluble Starch | 1.0 |
| Organic pH Indicator | |
| Bromcresol Purple | 0.0024 |

4. The subject matter of claim 3, in which such specified wavelengths for evaluations of sterilizing effectiveness, by measurements of peak absorption of electromagnetic radiation selected from the group consisting of:
   (a) about 260 nm, for an early load release evaluation;
   (b) about 325 nm for an early load release evaluation,
   (c) about 430 nm for a delayed evaluation after such spore culturing period, and indicating an increase in acidity such that added sterilizing efforts should be required, and
   (d) about 590 nm for an early load release evaluation, and a delayed evaluation after such spore culturing period, each indicating load release.

* * * * *